(12) United States Patent
Daniels et al.

(10) Patent No.: US 12,128,080 B2
(45) Date of Patent: Oct. 29, 2024

(54) ELECTROSPUN FIBERS CONTAINING NANODISPERSIONS AND THEIR USE FOR THE TREATMENT OF WOUNDS

(71) Applicant: NSC PHARMA GMBH & CO. KG, Greven (DE)

(72) Inventors: Rolf Daniels, Rottenburg (DE); Francis Karnau Mwiiri, Tübingen (DE)

(73) Assignee: NSC PHARMA GMBH & CO. KG, Greven (DE)

( * ) Notice: Subject to any disclaimer, the term of this patent is extended or adjusted under 35 U.S.C. 154(b) by 177 days.

(21) Appl. No.: 17/254,373

(22) PCT Filed: Jun. 17, 2019

(86) PCT No.: PCT/IB2019/055028
§ 371 (c)(1),
(2) Date: Dec. 21, 2020

(87) PCT Pub. No.: WO2019/243988
PCT Pub. Date: Dec. 26, 2019

(65) Prior Publication Data
US 2021/0268054 A1    Sep. 2, 2021

(30) Foreign Application Priority Data
Jun. 19, 2018 (EP) .................. 18178665

(51) Int. Cl.
| | | |
|---|---|---|
| *A61K 36/185* | (2006.01) | |
| *A61K 9/107* | (2006.01) | |
| *A61K 9/12* | (2006.01) | |
| *A61K 9/70* | (2006.01) | |
| *A61K 31/015* | (2006.01) | |
| *A61K 31/047* | (2006.01) | |
| *A61K 31/19* | (2006.01) | |
| *A61K 31/215* | (2006.01) | |
| *A61K 47/24* | (2006.01) | |
| *A61K 47/32* | (2006.01) | |
| *A61K 47/44* | (2017.01) | |
| *A61P 17/02* | (2006.01) | |
| *D01D 5/00* | (2006.01) | |
| *D04H 1/728* | (2012.01) | |

(52) U.S. Cl.
CPC ......... *A61K 36/185* (2013.01); *A61K 9/1075* (2013.01); *A61K 9/122* (2013.01); *A61K 9/7015* (2013.01); *A61K 31/015* (2013.01); *A61K 31/047* (2013.01); *A61K 31/19* (2013.01); *A61K 31/215* (2013.01); *A61K 47/24* (2013.01); *A61K 47/32* (2013.01); *A61K 47/44* (2013.01); *A61P 17/02* (2018.01); *D01D 5/0007* (2013.01); *D04H 1/728* (2013.01); *D10B 2509/022* (2013.01)

(58) Field of Classification Search
CPC .... A61K 36/185; A61K 17/02; A61K 9/1075; A61K 9/122; A61K 9/7015; A61K 31/015; A61K 31/047; A61K 31/19; A61K 31/215; A61K 47/24; A61K 47/32; D01D 5/0007; D04H 1/728; D10B 2509/022
See application file for complete search history.

(56) References Cited

U.S. PATENT DOCUMENTS

| | | | |
|---|---|---|---|
| 7,871,642 B2 * | 1/2011 | Supersaxo | ........... A61K 9/4866 264/4.1 |
| 9,352,041 B2 | 5/2016 | Scheffler | |
| 2010/0254961 A1 | 10/2010 | Nishio | |

FOREIGN PATENT DOCUMENTS

| | | | |
|---|---|---|---|
| EP | 2363108 A1 | | 9/2011 |
| RU | 2322998 | * | 4/2008 |
| WO | 0956853 A2 | * | 11/1999 |
| WO | 2011/075623 A1 | | 6/2011 |
| WO | 2018/017576 A1 | | 1/2018 |

OTHER PUBLICATIONS

Okuda et al. J. Biomaterials Science, Polymer Edition 24(10) 2013; 1277-1290.*
Ep-0956853 Eng. 1999.*
P.M. Newmann et al.: "Gelatin-based sprayable foam as a skin substitute", Journal of Biomedical Mateirals Research, vol. 15, No. 1, Jan. 1, 1981, pp. 9-18.
Payam Zahedi et al. "A review on wound dressing with an emphasis on electrospun nanofibrous polymeric bandages" Polymers for Advanced Technologies, vol. 21, Jan. 2010, pp. 77-95.

* cited by examiner

*Primary Examiner* — Shirley V Gembeh
(74) *Attorney, Agent, or Firm* — Stuart H. Mayer; Kaplan Breyer Schwarz LLP

(57) ABSTRACT

The present invention relates to compositions based on nanodispersions which are preferably further processed to electrospun fibers comprising such nanodispersions. The nanodispersions may optionally contain birch bark extract. The electrospun fibers can be used in particular for the treatment of wounds. For this purpose the compositions containing electrospun fibers are preferably applied as such or in a spray or a foam.

9 Claims, 2 Drawing Sheets

Figure 1: 10%PVA nanofibers containing phospholipid-birch bark extract nanodispersions (60% / 40%)

ELECTROSPUN FIBERS CONTAINING NANODISPERSIONS AND THEIR USE FOR THE TREATMENT OF WOUNDS

The present invention relates to compositions based on nanodispersions which are preferably further processed to electrospun fibers comprising such nanodispersions. The nanodispersions may optionally contain birch bark extract. The electrospun fibers can be used in particular for the treatment of wounds. For this purpose the compositions containing electrospun fibers are preferably applied as such or in a spray or a foam.

US 2010/0254961 A1 describes water-soluble electrospun sheets and their use in medicine.

In her doctoral thesis M. Laszczyk, Freiburg, 2007, described triterpene dry extract from birch bark (betula alba cortex) and its potential pharmaceutical use. Birch bark extract has antibacterial activity and also activity against plasmodia or viruses. Moreover, it is anti-inflammatory and helpful in the healing of wounds. Even anti-tumoral activity has been described. Despite those highly desirable properties the use of the birch bark extracts has been hindered by the difficulties in preparing suitable pharmaceutical formulations. The reason for those difficulties can be seen in the low solubility of the extract in water and also in problems when the extract is dissolved in oils due to the formation of gel structures.

In WO 2018/017576 betulin-containing water-in-oil foams comprising solid birch bark extract dispersed in one or more non-polar liquids are disclosed. This foam is an emulsified oleogel which comprises solid birch bark extract in water-in-oil emulsion.

The present invention relates to an improved pharmaceutical formulation containing electrospun fibers, optionally containing birch bark extract. The human skin serves as a barrier between the body and the environment. Therefore, it is prone to microbial, thermal, mechanical and chemical threats which can cause acute or chronic wounds. Triterpenes from the outer bark of birch are known for various pharmacological effects including enhanced wound healing. Polymeric nanofibers made from biodegradable and biocompatible synthetic or natural polymers have been utilized to develop drug delivery systems to treat various ailments and one of the potential areas to use them is medicated wound dressing. Hence, one object of the present invention is to use birch bark dry extract which has been recently clinically proved to speed up wound healing and to provide a bioactive nanofiber wound dressing. Sub-micron O/W-emulsions containing the active substance birch bark dry extract are first produced via high-pressure homogenization [HPH] process and lecithin-based phospholipids as emulsifier. In one embodiment the emulsions are blended with commercially available biodegradable and biocompatible polymers to form nanofibers intended for wound therapy using electrospinning technology. The preparation processes and emulsion compositions (e.g. polymer/birch bark dry extract/phospholipid/sunflower oil) influence the drug release behavior of the scaffolds, together with their structural morphology, surface and thermal properties.

Birch bark extract can thicken oils which results in so-called oleogels. An oleogel is a flexible and deformable system comparable to a hydrogel. Contrary to the hydrogel an oleogel is based on a lipophilic phase. Such oleogels may show a thixotropic behaviour which means that by quick stirring the viscosity is decreased whereas without applied shear forces the viscosity is higher. Although there may be some applications where thixotropic properties are helpful it is for pharmaceutical purposes not always convenient. It is therefore an object of the present invention to provide alternative formulations of birch bark extract which are suitable for pharmaceutical applications.

One object of the present invention is to provide alternative pharmaceutical formulations which have advantageous properties regarding bioactivity, handling and acceptance of the patients.

Birch bark extracts have a high content of triterpenes which are biologically active secondary plant metabolites. Their various pharmacological properties like anti-inflammatory, anti-viral, anti-cancer activity and wound healing effects are well investigated and specified in the literature. These substances are widely distributed in plants but only the outer bark of the white barked birches contains up to 34% (w/w) betulin, a pentacyclic, lupan type triterpene with two polar hydroxyl groups located on opposite sides of the molecule. A well characterized commercially available triterpene dry extract from the outer bark of birch (TE) contains about 80% (w/w) betulin. This extract is obtained by accelerated solvent extraction with n-heptane. Further disclosed constituents of the dry extract are lupeol (LU), erythrodiol (ER), betulinic acid (BA) and oleanolic acid (OA). However, the poor solubility of these triterpenes in polar and non-polar solvents might limit their therapeutic application due to a poor bioavailability. For the time being, available topical application forms are oleogels and cosmetic water-in-oil creams (e.g. Imlan Creme pur, Birken AG). An oleogel containing sunflower oil received a European marketing authorization in January 2016.

Birch bark is a low-value waste product which is generated in huge amounts in the forest industry. Therefore, the starting material for the birch bark extract is easily available at low costs.

The birch bark consists of inner birch bark and outer birch bark. The inner birch bark is more dense and granular than the outer birch bark while the outer birch bark is more flexible and fibrous than the inner birch bark. The outer birch bark is white in colour, thin, tough and has a lower water content compared to the inner birch bark. The inner birch bark is darker in colour and a separation of the fragments of the outer birch bark from the fragments of the inner birch bark leads to an increase in the yield of the desired birch bark extract. The outer birch bark contains a high concentration of interesting chemical components which can be extracted for example with supercritical fluids whereby alkanes with $C_5$-$C_{10}$ preferably heptan are preferred.

Several different methods of extraction are known. In one process the triterpenes are extracted from the birch bark in hot n-heptane whereby the temperature shall be above about 110° C. When the hot n-heptane is cooled the triterpenes crystallize and can be obtained by filtration and drying the crystals. It is also possible to use other extraction fluids or to use $CO_2$ for extraction. Since the birch bark extract is a natural product the composition of the single components depends strongly on several factors like species of the birch from which the bark is obtained, mode of preparation of the birch bark extract and subsequent purification steps.

The birch bark extract contains chemical constituents which are useful in pharmaceutical applications since antiviral, antibacterial and anti-inflammatory activity has been reported. Therefore, birch bark extracts can be used as antibacterial or antifungal agents and in wound healing.

Depending on the provenience and the method of production the birch bark extract contains several components. The main component is betulin which is usually present in the extract in an amount of about 75 to 85 wt. %. Lupeol is present in an amount of about 1.5-2.8 wt. % and betulonic acid is present in an amount of about 3.0-4.5 wt. %. Minor concentrations of erythrodiol, oleanolic acid and betulinic acid methyl ester are present. Furthermore, there are also some minor components in the birch bark extract like betulin aldehyde, ursolic acid, α- and β-boswellic acid and others. It goes without saying that all components must sum up to 100% whereby, however, minor traces of the solvent used for extraction may be present in the extract.

The birch bark extract may cause problems in the preparation of pharmaceutical formulations since the components of the birch bark extract can build via hydrogen bonds three-dimensional structures which cannot easily be brought into a suitable form with sufficient bioavailability. Particles of variable size and gel formation may occur which makes the preparation of a suitable pharmaceutical formulation difficult, because the pharmaceutical component cannot be released in a controlled manner. It may for example be difficult to apply a thin and equally distributed layer of the oleogel on a wound.

According to the invention a nanodispersion of birch bark extract is provided which shows superior bioavailability. The nanodispersions according to the present invention are preferably prepared by homogenizing a pre-emulsion. The pre-emulsion contains the birch bark extract, a pharmaceutically acceptable oil, an emulsifying agent and an aqueous phase. The oil can be any suitable pharmaceutically acceptable oil like castor oil, corn oil, coconut oil, linseed oil, olive oil or peanut oil whereby sunflower oil is preferred. Such oils are usually purified to comply with pharmaceutical standards.

DETAILED DESCRIPTION OF THE INVENTION

Figure 1:
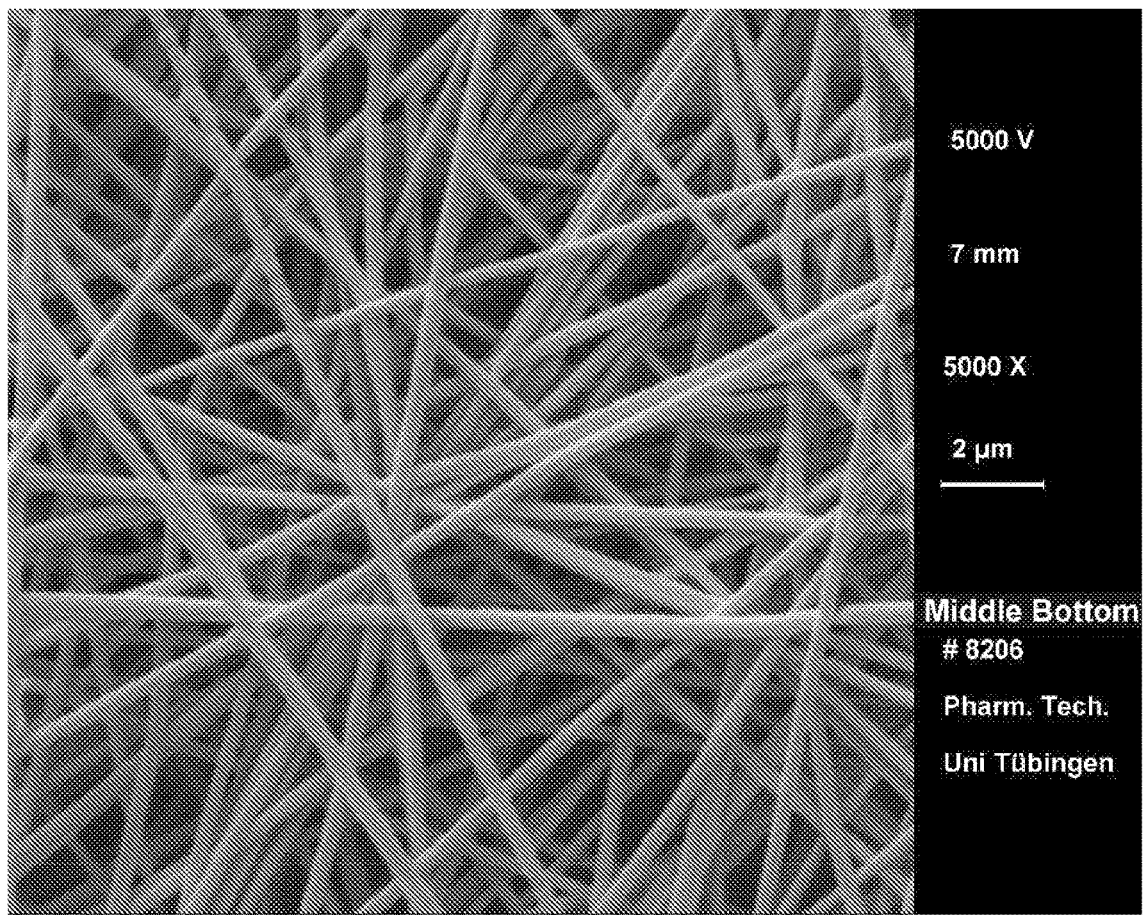
FIG. 1 illustrates 10% PVA nanofibers containing phospholipid-birch bark extract nanodispersions (60%/40%) in accordance with the invention.

In a preferred embodiment the O/W emulsion consists of four important constituents, including the active substance (birch bark dry extract), phospholipids as emulsifiers, oil phase, and water phase. Composition and processing conditions are expected to have a significant impact on the characteristics of these sub-micron dispersions. Also, the properties of the emulsion-electrospun nanofibers will be highly governed by characteristics of the triterpene sub-micron-emulsions. Apart from that, a controlled drug release can be gained through variation of the dispersion properties. Electrospinning of emulsions containing phospholipids is not commonly practised.

The emulsifying agent as used according to the present invention is a phospholipid. The phospholipids ensure the miscibility at liquid-liquid and liquid-solid interfaces and may be derived from commercial lecithin. Phospholipids are essential constituents of the protoplasm of animal and plant cells. In general, different types of phospholipids like native and/or hydrated phospholipids can be used. The preferred phospholipids used according to the present invention are phosphatidylcholine, phosphatidylethanolamine, phosphatidylinositol, phosphatidic acid and phosphatidylserine and mixtures thereof. Phospholipids which are preferably used according to the invention are commercially available for example under the designation "Phospholipon® 90H". This is mainly hydrogenated phosphatidylcholine, but also other commercially available products of phospholipids for pharmaceutical purposes can be successfully used.

In the nanoemulsion the phospholipid is present in an amount of 0.01 to 8% by weight, preferably 0.1 to 5.0% by weight related to the weight of the nanoemulsion. In an especially preferred embodiment the nanoemulsion contains about 0.5% by weight of birch bark extract.

In the first step of the preparation of a nanoemulsion, the pre-emulsion consisting of the birch bark extract, an oil, preferably a pharmaceutically acceptable oil like sunflower oil or linseed oil is mixed with the phospholipid and water in a homogenizer. This mixture is then further treated to reduce the particle size of the single droplet particles from an average of a droplet particle size of 2-10 μm to a submicron size of about <1 μm and preferably below 400 nm. This can be done by high shear or ultrasonic emulsification which are very efficient in reducing the droplet size. Alternatively, high pressure homogenization can be used whereby a high pressure homogenizer/piston homogenizer is used to produce nanoemulsions of extremely low particle size down to several nanometers.

An advantage of the nanodispersion is that the pharmaceutically active components of the birch bark extract are distributed into extremely fine particles or droplets which results in an improved bioavailability. Such a nanodispersion can be directly applied to wounds or infected skin for example by spraying onto the affected area of the body. The nanodispersion according to the present invention is superior compared with an oleogel with regard to handling properties. It is a fluid which can even be sprayed or distributed onto infected skin areas.

Electrospinning has attracted increasing attention, because it allows drug incorporation into nanofibers by simply mixing the active compound with the polymer solution and subsequent processing using adequate equipment. This process is well known in the art and does therefore not have to be explained further at this point. The produced fleece has unique properties, such as high porosity, high encapsulation efficiency and high surface area to volume ratio thus high drug loading. In addition, wound dressing made from electrospun fibers mimic the native extracellular matrix in human tissues hence facilitate cell proliferation, improve gaseous exchange, removal of exudate, act as a physical barrier against entry of microorganisms and dehydration during wound healing. Polyvinyl alcohol (PVA), a hydrophilic polymer, is preferably used and has been already approved by the FDA for human use. PVA polymers have unique properties such as good chemical resistance, thermal stability, biodegradability, biocompatibility and non-toxicity which make it suitable to be electrospun as polymer-drug carrier for wound dressing.

However, encapsulation of birch bark dry extract into nanofibers may cause difficulties. For instance, earlier studies showed that due to their unique structure the particle sizes of the dry extract cannot be grinded to reach sufficiently small particles even when high energy dispersion techniques, e.g. sonication or high-pressure homogenization, were used with aqueous and organic suspensions of the material. This could be solved through processing of sub-micron emulsions with birch bark dry extract as the active substance through homogenization and use of phospholipids as emulsifier. This phenomenon presumably seems to be directly linked to the use of phospholipids as emulsifiers. In this context, it was found that the interfacial tension of mixtures of the triterpene extract and the phospholipids surprisingly reveal cooperative effects. Processing mixtures of triterpene extract, phospholipid, and oil with a high-pressure homogenizer yielded submicron-sized dispersions (nanodispersions). These submicron droplets may serve as drug carriers to encapsulate poorly soluble drugs. This can increase the solubility of the lipophilic birch bark dry extract leading to an improved local bioavailability. Moreover, the phospholipids will also help to stabilize the lipophilic birch bark dry extract in O/W emulsions thereby increasing its compatibility to the hydrophilic PVA polymer solution prior to electrospinning. Furthermore, since the electrospun nanofibers are usually also in the sub-micron range, the production of submicron emulsions will enhance a better encapsulation and uniform distribution of the birch bark dry extract throughout the polymer matrix.

Alternatively, the preparation of a nanoemulsion can be made as follows: The pre-emulsion consisting of a mixture of one or more phospholipids and water is treated in a homogenizer. This mixture is then further treated to reduce the particle size of the single droplet particles from an average of a droplet particle size of 2-10 μm to a submicron size of about <1 μm and preferably below 400 nm. This can be done by high shear or ultrasonic emulsification which are very efficient in reducing the droplet size. Alternatively, high pressure homogenization can be used whereby a high pressure homogenizer/piston homogenizer is used to produce nanoemulsions of extremely low particle size down to several nanometers.

As described before the phospholipids in the nanodispersion are distributed into extremely fine particles or droplets which results in an improved bioavailability. Such a nanodispersion without birch bark extract can be directly applied to wounds or infected skin for example by spraying onto the affected area of the body. It is a fluid which can even be sprayed or distributed onto infected skin areas.

Furthermore it can be converted into a foam which is easy and almost touchless to apply to the skin and which is preferred by many patients.

For such application the nanodispersion is simply filled into a standard aerosol can, a propellent gas such as propane/butane, $N_2O$, dimethyl ether or the like is added (2-20 weight %) and the can is closed with a standard foam head.

In a preferred aspect of the present invention the nanodispersion is further processed into electrospun fibers whereby the advantage of the nanodispersion, namely the fine dispersion and high bioavailability of the birch bark extract can be saved for a longer period of time. Another advantage of this embodiment is the easy handling of such fibers. Electrospun fibers can be easily used to form a fleece or a net structure which can be applied to wounds. There are many occasions where such fleeces or nets for the treatment of wounds are very helpful. If, for example, a larger area of the epidermis has been injured or even removed, for example in the case of a traffic accident or after burning, such fleece structures are very helpful. Alternatively, in particular with elderly people, there are frequently severe problems of wounds for example caused by decubitus. This type of wound is difficult to treat and may cause serious discomfort. For such wounds a fleece having antibacterial and antiviral activity is very helpful, in particular when the fabric structure must not be removed since the fibers are dissolved and absorbed by the body.

In a preferred embodiment of the invention the birch bark extract is in the first step brought into a nanodispersion as described hereinbefore. Then this nanodispersion is converted to an electrospun fiber which comprises a fiber-forming agent. Preferably the nanodispersion of the birch bark extract is integrated with, admixed with, comingled with or intermixed with the carrier. Specifically, the electrospun fiber contains both the pharmaceutically active agent (birch bark extract) and the carrier together in a homogenous manner.

During comparative investigation of the electrospun fibers containing both the pharmaceutically active agent (birch bark extract) and the carrier together in a homogenous manner it has been found that, surprisingly, electrospun fibers made from phospholipid containing nanodispersions without any birch bark extract have excellent properties and can be used for the production of compositions for wound treatment. Accordingly, further objects of the invention are electrospun fibers made from phospholipid containing nanodispersions being essentially free from birch bark extract und their use for the manufacture of compositions for wound treatment.

Electrospinning is a process of producing fibers whereby the diameters of the fibers can be in the range of from about 50 nm to about 2 μm, preferably in the range of 200 nm to 800 nm. The process comprises the application of a high voltage to a polymer solution in order to produce a polymer jet. As the jet travels through the air the jet is elongated under repulsive electrostatic force whereby nanofibers are produced.

According to the invention a nanodispersion containing phospholipids is formed and mixed with a polymer. Optionally, the birch bark extract is first solubilized into a nanodispersion which is then mixed with a suitable polymer. The nanodispersion-polymer solution (with or without birch bark extract) is ejected for example with a syringe pump and the polymer jet moves under a high voltage field to a target where the fibers can be collected. In such fibers, extremely small droplets of the nanodispersion are dispersed within the carrier polymer. The nanodroplets of the birch bark extract are finely distributed in the polymer matrix whereby also an ultra-homogenization step may be helpful. Since the droplets are very small and evenly distributed within the electrospun fiber, the nanodispersion has been transferred to a solid state which allows a controlled release of the active components of the birch bark extract. The electrospun fibers maintain the bioavailability of the nanodispersion.

The polymers usable for the preferred embodiment must be pharmaceutically acceptable. Such polymers may be selected from polyethylene oxide, polyvinyl alcohol, polyvinyl acetate, polyvinylpyrrolidone, hyaluronic acid, alginates, carrageenan, cellulose derivatives such as carboxymethylcellulose, sodium methylcellulose, ethylcellulose, hydroxy-ethylcellulose, hydroxpropylcellulose, hydroxypropylmethylcellulose, hydroxypropyl-methylcellulose phthalate, cellulose acetate phthalate, starch derivatives such as hydroxyethyl starch, sodium starch glycolate, chitosan and derivatives, albumin, gelatin, collagen, polyacrylates and derivatives thereof. Particularly preferred are such polymers which are easily dissolvable without undesired properties on a wound. Particularly preferred is polyvinyl alcohol or poly(lactide-co-glycolide).

It is an advantage of the electrospun fibers according to the present invention that the polymers which form together with the nanodispersion the electrospun fibers dissolve in the wound and there is no need for removal of the scaffold. Depending on the specific needs of the electrospun fiber the time of dissolution can be adjusted by selecting the suitable polymer or blend of the polymers. It is well-known for example that by changing the ratio of the monomers in a polylactide/polyglycolide co-polymer the dissolution time in the body (or on the wound) can be adjusted. By selecting two or three different polymers and mixing them together to a copolymer, the properties of the matrix of the fiber may be precisely adjusted. The process of electrospinning for the preparation of nanofibers for a fabric or fleece for medical purposes is known. In the electrospinning process some parameters can be easily adjusted whereby the properties of the electrospun fibers can be influenced. The selection of a suitable voltage has an effect on the properties of the fiber as well as the viscosity of the nanodispersion mixed with the polymer. Moreover, the concentration of the nanodispersion in correlation with the concentration of the polymer, the molecular weight of the polymer, the surface tension and the homogeneity and the conductivity of the solution have essential effect on the property of the electrospun fibers.

The parameters such as feed (flow) rate, applied voltage, tip of syringe-to-collector distance have to be optimized and the ambient parameters, in particular temperature, humidity and the pressure have to be controlled. Depending on the device for electrospinning the fibers, the parameters can be adjusted in order to obtain the desired properties of the fibers which is optimized for the intended field of application.

Since the material used for the formation of the electrospun fibers is liquid it may be advantageous to remove the liquid at least partially after the fiber is spun. This may be obtained by adding high volatile liquids like alcohol or ether or by applying a reduced pressure in the chamber where the nanodispersion (optionally containing birch bark extract) and polymer is spun. Under reduced pressure the liquid evaporates, and the fiber is dried and becomes stiffer.

The electrospun fibers comprising the nanodispersion optionally containing birch bark extract can advantageously be used for the treatment of wounds. Such fibers can easily be transferred into a fleece of a desired thickness and can easily be sterilized. Such a sterile fleece or mat or net has a high surface area to volume ratio which results in a high drug loading capacity. Another advantage of the electrospun microfibers is the high porosity of the fabric which may act as a physical barrier against microorganisms. Therefore, the affected skin area may heal very well whereby the invasion of undesired microorganisms from the environment is prevented.

Many wound dressings in the market containing active agents like hydrocolloids or silver dressings which are often used on wound healing have shown negative effects like allergic contact dermatitis and use of dressings loaded with antibiotics bears the risk of developing resistance in bacteria against antibiotics.

Therefore, one object is to develop a dressing (optionally loaded with birch bark extract) with a sustained drug release of about 2 to about 10 days, preferably about 5 days which is suitable for human use on wound healing with effective therapy even after long term usage. Since all the components are biocompatible and biodegradable in human body, an invasive and/or traumatic intervention for dressing removal like in deep wounds is unnecessary. Furthermore, sustained drug release could lead to less frequent dressing changes which is painful especially in treatment of chronic wounds and thereby resulting to a better patient compliance.

The nanofibers according to the invention have also other advantages like excellent performance in cell adhesion, migration, proliferation and differentiation and the analogous physical properties of extracellular matrix. Another advantage of the electrospun fibers according to the present invention is the sustained release of the birch bark extracts over time. Since the droplets derived from the nanodispersion of the birch bark extract are distributed within the electrospun fibers the pharmaceutically active substances are released depending on the dissolution of the electrospun fiber.

Selecting the appropriate polymer forming the fiber is another measure to determine the speed of the dissolution. Some polymers dissolve quickly whe-reas others remain intact for a longer time. When the fibers are dissolved the droplets entrapped within the fibers are liberated and an optimal concentration of the compounds of the birch bark extract is provided exactly at the place where it is needed.

Depending on the intended use, an appropriate ratio of the nanodispersion to the polymer is used. Usually the ratio of the nanodispersion to the polymer ranges from about 1.0 to 60 parts by weight of nanodispersion to 99 to 40% by weight of the polymer, preferably from 5 to 50% nanodispersion to 95 to 50% polymer and particularly preferred from 25 to 45% nanodispersion to 55 to 75% of the polymer.

Moreover, it has been found that even the electrospun fibers optionally containing birch bark extract can be converted into a foam. As described earlier such foam is easy and almost touchless to apply to the skin and is preferred by many patients.

In order to provide such foam formulation electrospun fibers have to be mixed with water under stirring to form a dispersion. This dispersion is then filled into a standard aerosol can, a propellent gas such as propane/butane, $N_2O$, dimethyl ether or the like is added (2-20 weight %) and the can is closed with a standard foam head. The foam which can be provided by such aerosol can is easy and almost touchless to apply to all kind of wounds, such as burning wounds, abrasion wounds or decubitus.

Further aspects of the invention are shown in the following Examples:

EXAMPLES

In the following examples, different nanodispersions having variable amounts of birch bark extract were used. The nanodispersions were mixed with a PVA solution and the mixture was electrospun. The different mixtures of Examples 1-4 are shown below.

|  | Example 1 | Example 2 |
| --- | --- | --- |
| Nanodispersion | Phospholipon 90 H 2.5%<br>sunflower oil 1.0%<br>birch bark extract 0.5%<br>Water 96.0% | Phospholipon 90 H 2.5%<br>sunflower oil 1.0%<br>Water 96.5% |
| PVA Solution | PVA 10%<br>Water 90% | PVA 10%<br>Water 90% |
| Electrospun mixture | Nanodispersion 40%<br>PVA Solution 60% | Nanodispersion 40%<br>PVA Solution 60% |

|  | Example 3 | Example 4 |
| --- | --- | --- |
| Nanodispersion | Phospholipon 90 H 8.0%<br>sunflower oil 10.0%<br>birch bark extract 5.0%<br>Water 77.0% | Phospholipon 90 H 8.0%<br>sunflower oil 10.0%<br>Water 82.0% |
| PVA Solution | PVA 10%<br>Water 90% | PVA 10%<br>Water 90% |
| Electrospun mixture | Nanodispersion 30%<br>PVA Solution 70% | Nanodispersion 30%<br>PVA Solution 70% |

The properties of the mat obtained with the mixture of Example 1 are shown in Table 1:

| Sample type | Content |
| --- | --- |
| Emulsion composition (wt %) | 2.5% Phospholipon 90 H: 1% sunflower oil: 0.5% birch bark extract and 96% water |
| Pre-emulsion droplet size (nm)/ polydispersity index | 3360/0.89 |
| Nanodispersions droplet size (nm)/ polydispersity index | 399.91/0.52 |
| 10% PVA/nanodispersions blend proportion (wt %) | 60%/40% |
| 10% PVA/nanodispersions (60%/40%) fleece fiber diameter range (nm) | 306-420 |
| 10% PVA fleece porosity with nanodispersions (%) | 87.34 |
| Pure 10% PVA fleece fiber diameter range (nm) | 482-863 |
| 10% PVA fleece porosity without nanodispersions (%) | 80.40 |

Applied voltage (kV): 15

An electron microscope picture of a 10% PVA nanofiber containing phospholipid birch bark extract nanodispersions (60%/40%) is shown in FIG. 1.

Example 5

In order to show the superior activity of the embodiments of the present invention a porcine ex vivo wound healing assay has been performed. Briefly, pig ears obtained from a slaughter house (for human consumption) were directly delivered after slaughtering to the laboratory, cleaned and disinfected. Thereafter, 6 mm punch biopsies were taken from the plicae of the ears and fat and subcutis were removed. Consequently, wounds were generated by the removal of the epidermis and upper dermis in a central area of 7.1 mm$^2$. Then, the so formed ex-vivo wound healing model was placed dermis-down on gauze in culture dishes and incubated air-liquid interface with Dulbecco's modified Eagle's medium supplemented with hydrocortisone, 2% fetal calf serum, penicillin and streptomycin. 4 cm$^2$ of the electrospun mat/5 μl of the oleogel were immediately applied after wounding and the models incubated for 48 h at 37° C. and 5% $CO_2$. Further steps involved shock freezing, cryostat sections of the central parts of the wound healing models were identified using a ruler in the microscope and by checking the total length of the wound during evaluation—were stained with hematoxylin and eosin. Wound healing process (reepithelialization) was assessed by measuring the distance between the wound margin and the tip of the regenerated epidermis with a microscope.

In the Example as control the wound has not been treated at all. As comparison with the prior art an oleogel was used. A slight improvement could be observed. Furthermore, a polyvinyl alcohol mat without birch bark extract (PVA mat) was used. It can be seen that the healing properties are better than in the control and even better than with oleogel.

When the polyvinyl alcohol mat contained birch bark extract, a significant improvement in the healing activity could be observed. This can be seen with 5% birch bark extract (TE) and more effectively with 0.5% birch bark extract (TE).

Figure 2:
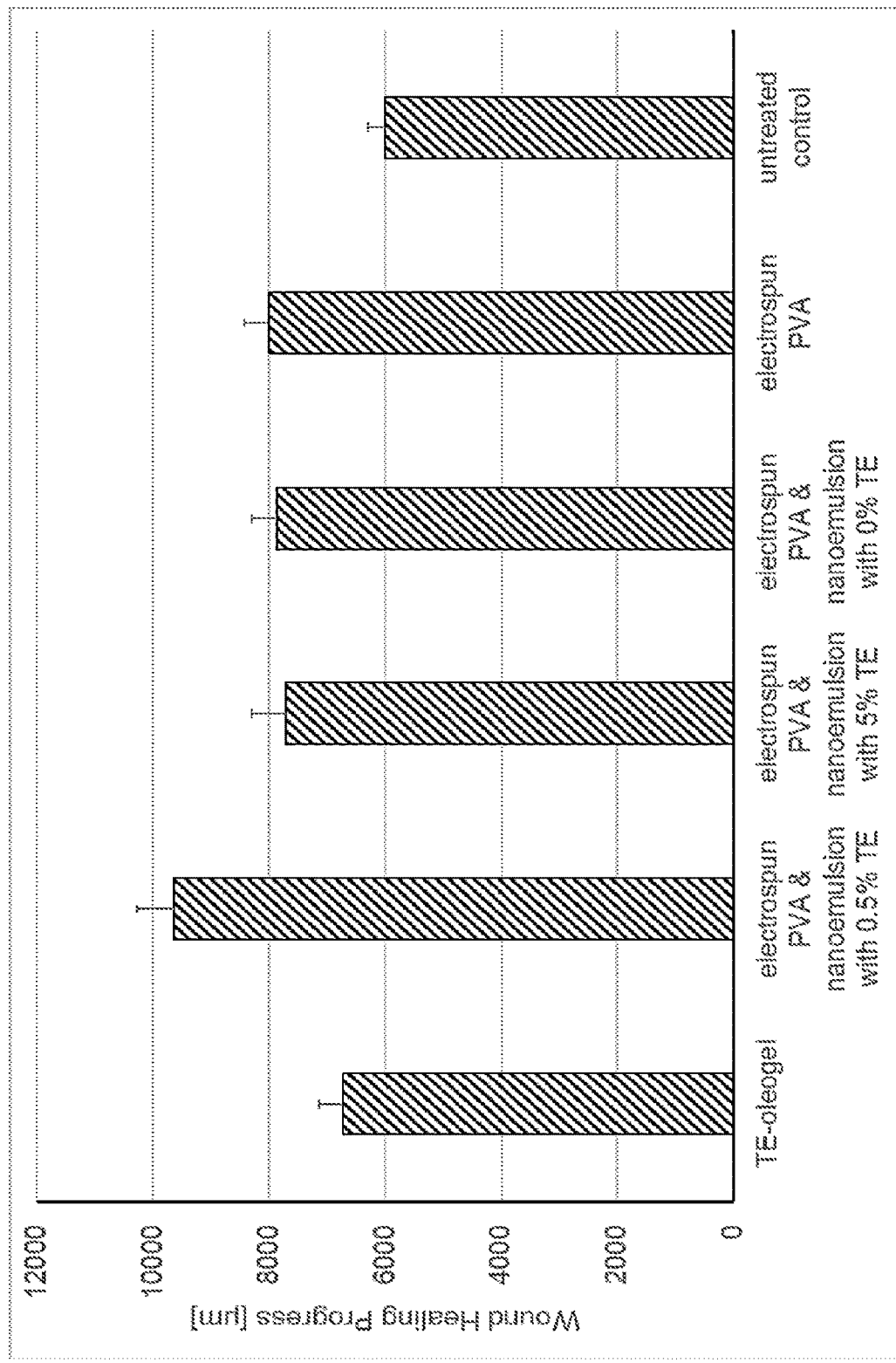
FIG. 2 illustrates an ex vivo wound healing array in accordance with the invention.

Example 6 a) In further experiments (results not shown in FIG. 2) the preparations according to Example 5 are compared with preparations being essentially free of birch bark extract. Surprisingly, the results achieved with preparations without birch bark extract are comparable to those with birch bark extract.

b) In additional experiments (results not shown in FIG. 2) the preparations containing electrospun fibers according to Examples 1-4 are converted into foam preparations which are used as described in Example 5. Again, the results achieved with foam preparations without birch bark extract are comparable to those foam preparations with birch bark extract.

The invention claimed is:

1. A method for treating wounds, comprising:
   providing a composition containing a nanodispersion which is stabilized with at least one phospholipid, wherein the nanodispersion is contained within an electrospun fiber integrated with a pharmaceutically acceptably polymer carrier and the at least one phospholipid mainly includes hydrogenated phosphatidylcholine, converting the electrospun fiber into a fleece or a foam; and
   applying the composition to the wound.

2. The method according to claim 1, wherein the nanodispersion further contains a birch bark extract.

3. The method according to claim 2, wherein the birch bark extract in the Nanodispersion comprises the following components calculated in percentage by weight:
   betulin 74-85 wt. %, lupeol 1.0-4.0 wt. %, betulinic acid 3.0-5.0 wt. %, erythrodiol 0.3-2.8 wt. %
   and other components, in particular derived from the birch bark like oleanolic acid, betulinic acid, methyl ester of betulinic acid 2-13 wt. %, whereby all components add up to 100 wt %.

4. The method according to claim 1, wherein the Nanodispersion is prepared by high shear or ultrasonic emulsification, or high pressure homogenization or microfluidization.

5. The method according to claim 1, wherein at least 95% of the particles of the Nanodispersion have a particle size below 1 pm.

6. The method according to claim 1, wherein the nanodispersion contains 0.1 to less than 5.0% by weight of birch bark extract.

7. The method according to claim 1, wherein the nanodispersion is prepared by mixing the phospholipid as emulsifying agent and water optionally with the birch bark extract with a pharmaceutically acceptable oil, and second to perform a high shear or ultrasonic emulsification or a high pressure homogenization of the mixture in order to obtain a nanodispersion whereby at least 95% of the particle droplets have a diameter of less than 1 pm.

8. The method according to claim 1, wherein the polymer is selected from the group comprising polyvinyl alcohol, poly(glycolide), polylactide-polyglycolide-copolymer, polyurethane, polyvinyl alcohol/cellulose acetate, silk fibroin, silk/chitosan, gelatin, collagen/chitosan.

9. The method according to claim 1, wherein the electrospun nanofiber contains 1.0-60 wt. % of the nanodispersion calculated on the basis of the total weight of the electrospun nanofiber.

* * * * *